(12) United States Patent
Cavaliere Vesely et al.

(10) Patent No.: US 6,582,695 B2
(45) Date of Patent: *Jun. 24, 2003

(54) SPHINGOMYELINASE COMPOSITIONS AND USE THEREOF

(75) Inventors: Renata Maria Anna Cavaliere Vesely, Milan (IT); Claudio De Simone, Ardea (IT)

(73) Assignee: VSL Pharmaceuticals Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/861,774

(22) Filed: May 22, 2001

(65) Prior Publication Data

US 2003/0077269 A1 Apr. 24, 2003

Related U.S. Application Data

(62) Division of application No. 09/308,366, filed on May 18, 1999, now Pat. No. 6,258,355.

(30) Foreign Application Priority Data

Nov. 22, 1996 (IT) .......................... RM96A0799

(51) Int. Cl.⁷ .................. A01N 63/00; A61K 38/46
(52) U.S. Cl. .................. 424/93.45; 424/93.44; 424/94.6; 435/853; 435/854; 435/855; 435/856; 435/857; 435/885

(58) Field of Search .................. 424/93.45, 93.44, 424/94.6; 435/853–857, 885

(56) References Cited

U.S. PATENT DOCUMENTS

| 4,158,607 A | * | 6/1979 | Kalinowski et al. .......... 195/62 |
| 4,524,136 A | | 6/1985 | Lee et al. |
| 5,851,782 A | | 12/1998 | Hannun et al. |
| 5,912,152 A | | 6/1999 | Hara et al. |
| 6,258,355 B1 | * | 7/2001 | Vesely et al. ............ 424/93.45 |

FOREIGN PATENT DOCUMENTS

| FR | 2 729 079 | 7/1996 |
| GB | 2 037 160 | 7/1980 |
| JP | 63-216813 | 9/1988 |

OTHER PUBLICATIONS

Kerscher et al. Eur. J. Dermatol. (1991), 1(1), 39–43.*

* cited by examiner

Primary Examiner—Irene Marx
Assistant Examiner—Vera Afremova
(74) Attorney, Agent, or Firm—Nixon & Vanderhye P.C.

(57) ABSTRACT

The use of sphingomyelinase to increase the levels of skin and mucosal ceramides, as well as dermatological and cosmetic compositions containing same which are suitable for topical application are disclosed.

4 Claims, 1 Drawing Sheet

SPHINGOMYELINASE COMPOSITIONS AND USE THEREOF

This is a Division of application Ser. No. 09/308,366, filed May 18, 1999, now U.S. Pat. No. 6,258,355.

The present invention relates to the use of sphingomyelinase to increase the levels of skin and mucosal ceramides, and dermatological and cosmetic compositions suitable for topical application containing same.

Ceramide (N-acylsphingosine) is a lipid metabolite which has recently been proposed as an important intracellular messenger released inside the cell within a few hours of stimulation with various agents or as a result of serum deprivation, and is related to cell blockade in the G0/G1 phase and apoptosis. Ceramide is currently regarded as a second messenger in the context of the sphingomyelin signal transduction pathway. It is released by sphingomyelin as a result of the effect of sphingomyelinases, which are forms of phospholipase C specific for sphingomyelin. Inside the cells, ceramide can influence growth and differentiation, regulate protein secretion, induce DNA fragmentation and apoptosis, and increase the synthesis and secretion of cytokines. The molecular mechanisms underlying these various different actions are as yet not entirely known. More is known, on the other hand, about extracellular agonists which cause the release of ceramide. Hydrolysis of sphingomyelin occurs rapidly after exposure of the cells to exogenous sphingomyelinase or to agonists which activate endogenous sphingomyelinases. Such agonists include TNF-$\alpha$, Fas ligand, interleukin 1-$\beta$, IFN-$\gamma$, 1$\alpha$, 25-dihydroxyvitamin $D_3$ and NGF.

Sfingomyelinase-containing cosmetic compositions are already known. Japanese Patent Publication 63 216813 discloses such a composition wherein the sphingomyelinase obtained therein aims at counteracting the physiological decrease of this enzyme in aging skin, thus promoting the conversion of sphingomyelin to ceramide which, in turn, brings about a beneficial moisturising effect on the skin.

The Japanese publication, however, does not disclose or in the least suggest that these compositions might be used therapeutically for treating dermatological disorders. Moreover, sphingomyelinase is obtained via a cumbersome and complex extraction method from tissues of higher animals, such as brain and liver.

The importance of ceramide in the skin metabolism shall be clearly apparent from what follows here below.

The main cellular constituents of the epidermis are keratinocytes, melanocytes, Langerhans cells, fibroblasts, endothelial cells and macrophages. Mono- and polymorphonuclear leukocytes can infiltrate the skin in the course of inflammation or tumours. The intracellular sp ace, on the other hand, consists mainly of neutral lipids, glyco-proteins, protein degradation products, desmosomes, active enzymes, products of sebaceous glands and ceramides. As long as this "bricks and mortar" structure is intact, the skin is endowed with both a protective layer and a selectively permeable filter.

During the differentiation process of the epidermis, which starts with cell division in the basal layers and ends with the death of keratinocytes and the development of the lipid barrier, the cells modify their lipid synthesis capability. The result is that the basal layer of the epidermis is characterized by phospholipids and cholesterol, whereas the outermost layer is characterized by cholesterol, free fatty acids, and, above all, ceramides. The lipids of the horny layer, the main component of which consists of sphingolipids, play a crucial role in maintaining the permeability barrier of the epidermis to water. The sphingolipids a re extruded from the lamellar bodies of the granular cells of the epidermis. Ceramides (sphingolipids), which make up 43–46% of the horny layer, are the main polar lipids of the horny layer and play a fundamental role in the barrier function of the skin against water leakage in cell adhesion and in the differentiation of the epidermis. Literature data indicate that ceramides are synthesised de novo in the epidermis via phospholipid-like intermediates. They are present in fairly high concentrations in the horny layer (up to 40% of total lipids).

Like the appearance of the surface of the skin, its functional properties also undergo changes with ageing. Ageing skin is characterized by a reduced water content in the horny layer associated with reduced transdermal leakage of water. It has been shown that the ceramide 2:sphingolipid ratio decreases with age. The drop in ceramide associated with ageing may be responsible for the dehydration of the skin which is observed in the course of ageing.

In addition, abnormal ceramide levels (deficiencies) have been detected in atopic eczema, dermatosis and dermatitis, in particular atopic dermatitis, and psoriasis. Recently, an inborn deficiency of ceramide 1 has been found in autosomal recessive sphingolipidosis. Equally well known are generalised forms of sphingolipidosis such as Fabry's disease, Gaucher's disease and Tay-Sachs disease. Sjögren-Larsson syndrome is associated with a deficiency of ceramide 1 and 6 with attendant destruction of the normal skin barrier.

In the light of the foregoing, it is obviously useful to maintain high levels of ceramide in the skin. It will additionally be understood that the use of sphingomyelinase proves advantageous also at mucosal level.

There are currently available on the market numerous products containing ceramides obtained by extraction methods or synthesis and used in dermatology and cosmetics. The topical external application of ceramides is proposed for remodelling the cutaneous lipid barrier altered by ageing, drugs, detergents, physical agents, etc. Such exogenous administration does not allow for the possibility that there may be qualitative and/or quantitative variations in ceramide due to age and anatomical site, seasonal factors and diseases. Clearly, then, the exogenous administration of ceramide acts only in an additive sense (endogenous+exogenous ceramide) and not in a modulatory sense (variations in ceramide according to season, anatomical site, possible disease processes in progress, etc.).

Surprisingly, we have now found that h levels of neutral, but not acid, sphingomyelinase are present in bacterial cell.

Consequently, one object of the present invention is to provide for the use of sphingomyelinase obtained from bacteria to produce dermatological or cosmetic compositions suitable for topical application in order to increase the level of ceramides in the skin and mucosa.

DETAILED DESCRIPTION OF THE INVENTION

Figure 1:
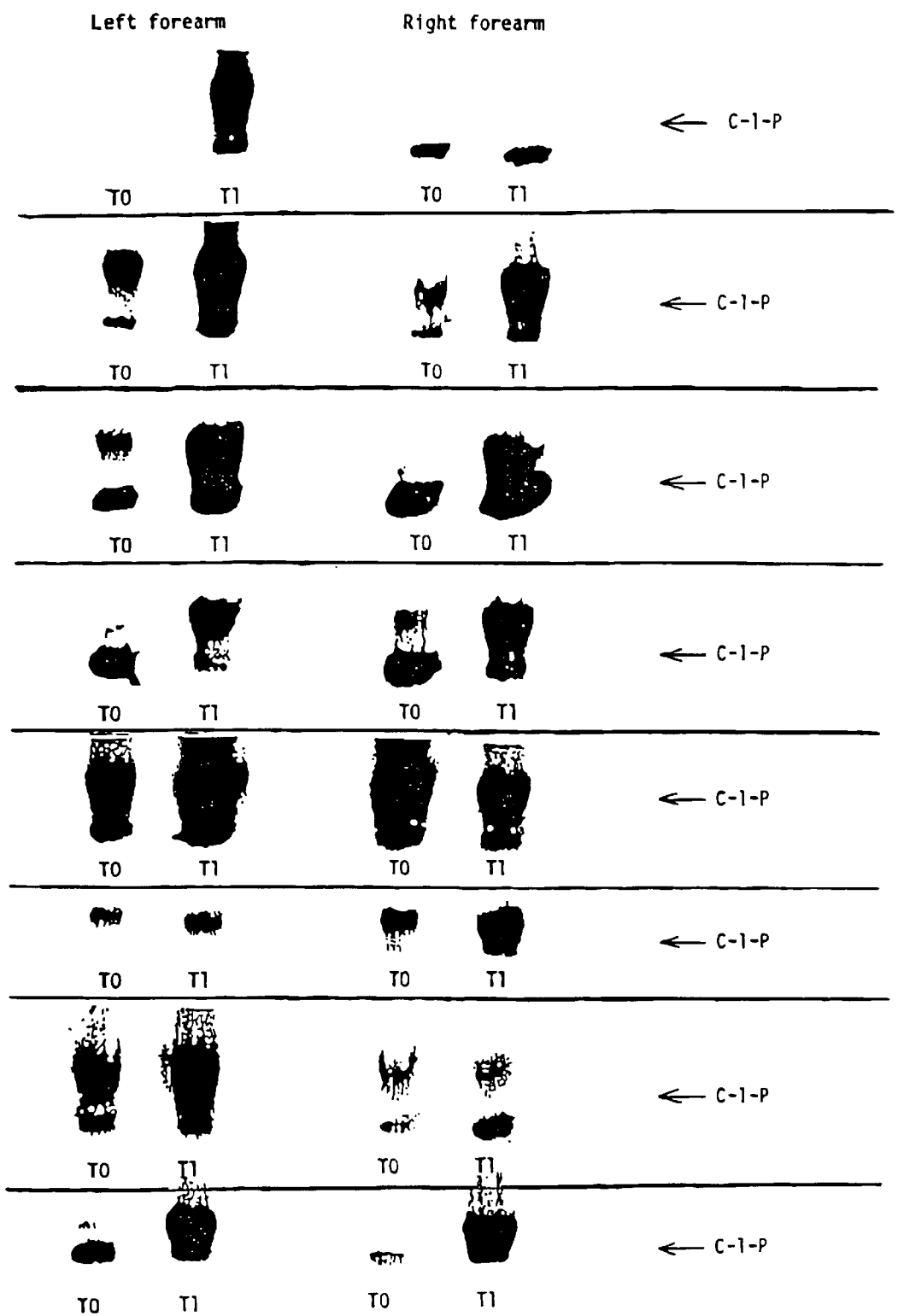
FIG. 1 Autoradiographs of ceramide levels.

According to the invention, the sphingomyelinase is preferably extracted from Gram-positive bacteria, Gram-negative bacteria, lactic bacteria or mixtures thereof. Lactic bacteria should preferably be chosen from among the following: *Lactobacillus acidophilus, Lactobacillus brevis, Lactobacillus buchneri, Lactobacillus casei, Lactobacillus catenaforme, Lactobacillus cellobiosus, Lactobacillus* crispatus, *Lactobacillus curvatus, Lactobacillus delbrueckii, Lactobacillus fermentum, Lactobacillus jensenii, Lactobacillus leichmanii, Lactobacillus minutus, Lactobacillus plantarum, Lactobacillus rogosae, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum, Bifidobacterium pseudocatenulatum, Bifidobacterium pseudolongum, Steptococcus lactis, Streptococcus raffinolactis* and *Streptococcus thermophilus*.

According to a preferred embodiment of the invention, the cells are used in the form of lyophilized or sonicated cells.

According to the present invention, the sphingomyelinase can furthermore be used as a cutaneous permeation or absorption enhancer, either alone or in admixture with other enhancers, for preparing pharmaceutical or cosmetic compositions suitable for transdermal administration.

A further object of the present invention is to provide dermatological or cosmetic compositions characterized by the fact that they contain an amount of sphingomyelinase effective for producing an increase in the level of ceramides in the skin or mucosa.

According to the invention, the sphingomyelinase contained in such compositions is preferably extracted from Gram-positive bacteria, Gram-negative bacteria, lactic bacteria or mixtures thereof. Lactic bacteria should preferably be chosen from among the following: *Lactobacillus acidophilus, Lactobacillus brevis, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus fermentum, Lactobacillus jensenii, Lactobacillus leichmanii, Lactobacillus minutus, Lactobacillus plantarum, Lactobacillus rogosae, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum, Bifidobacterium pseudocatenulatum, Bifidobacterium pseudolongum, Steptococcus lactis, Streptococcus raffinolactis* and *Streptococcus thermophilus*.

According to a preferred embodiment of the invention the cells contained in the compositions are in the form of lyophilized or sonicated cells.

The dermatological or cosmetic compositions of the invention shall preferably comprise from $1 \times 10^2$ to $1 \times 10^{15}$ CFU of lactic bacteria per gram of composition.

The dermatological or cosmetic composition of the invention may also-contain exogenous ceramide or products containing exogenous ceramide, sphingomyelines, fatty acids, cholesterol, ceramidase inhibitors, protease inhibitors, immunomodulators, vitamins, growth factors, surfactants, emulsifiers, stabilizers, lipids, rheological additives, humidifiers, antioxidants, preservatives, colouring agents, lakes, pigments, auxiliary substances (e.g. acids, bases, propellants) and functional substances (astringents, antiseborrhoeic agents, anti-dandruff agents, deodorants, skin purifiers, keratogenous agents, moisturizers, anti-xerosis agents, smoothing agents, screens, sunscreens, pigmenting agents, antidepigmenting agents, emollients, restorers, eutrophic agents, anti-wrinkle agents, antiradicals, stiffeners, anti-stretch-mark agents, vasoprotectors, anti-skin-rash agents, soothing agents, anti-cellulitis agents, tonifying agents, stimulants, hypereluting agents, epilators, nail protectors).

Lastly, the dermatological or cosmetic compositions of the invention can be formulated in the form of liquid, semiliquid, semisolid, solid or powder products, e.g. in the form of creams, ointments, lotions, capsules, pearls, ovules, mascara, eyewashes, toothpaste, mouthwashes, lipsticks, liposomes, soap, shaving soap, tonics, douches, enteroclysis solutions, shampoos, anti-dandruff preparations, impregnated and/or medicated bandage or gauze, patches, medicated emulsions, transdermal gels or patches.

To confirm the ability of these bacteria to induce the generation of ceramide in the skin, the following experiment was conducted, based on the detection of neutral sphingomyelinase, the enzyme responsible for generating ceramide in human skin.

Methods

Assay of Neutral and Acid Sphingomyelinase in Lactic Bacteria 10 mg of lyophilized *Streptococcus therrnophilus* were resuspended in 500 $\mu$l of buffer containing HEPES 20 mM, pH 7.4, $MgCl_2$ 10 mM, EDTA 2 mM, DTT 5 mM, $NA_3VO_4$ 0.1 mM, $Na_2MoO_4$ 0.1 mM, p-nitrophenylphosphate 30 mM, $\beta$-glycerophosphate 10 mM, ATP 750 mM, PMSF 1 $\mu$M, leupeptin 10 $\mu$M, pepstatin 10 $\mu$M (Sigma Chemical Co.) and 0.2% Triton X-100 (for the assay of neutral SMase activity) or 500 $\mu$l of 0.2% Triton X-100 (for the assay of acid SMase activity). The samples thus prepared were then submitted to lysis by sonication (for 1 min and 50 sec, alternating 10 sec of sonication with 10 sec of rest) using Vibracell sonicator (Sonic and Materials Inc., Danbury, Conn.). The sonicated samples were then centrifuged for 30 min at 14,000 rpm, at 4° C., the supernatant was removed and the protein concentration determined using the Bio-Rad Laboratories kit (Richmond, Calif.).

100 $\mu$g of sample were incubated for 2 hours at 37° C. in a buffer (50 $\mu$l final volume) containing HEPES 20 mM, $MgCl_2$ 1 mM, pH 7.4, and 2.25 $\mu$l of [N-methyl-$^{14}$C] sphingomyelin (SM) (0.2 $\mu$Ci/ml, a.s. 56.6 mCi/mmol, Amersham).

To measure the activity of acid sphingomyelinase, 100 $\mu$g of bacterial lysate were incubated for 2 hours at 37° C. in a buffer (50 $\mu$l final volume) containing sodium acetate 250 mM, EDTA 1 mM, pH 5.0, and 2.25 $\mu$l [N-methyl-$^{14}$C]SM. The reaction was blocked by the addition of chloroform:methanol:acetic acid (4:2:1). The phospholipids were extracted, analysed on plates by TLC and hydrolysis of SM quantified by means of autoradiography and liquid scintillation. The SMase present in the sonicated bacteria was indicated as Units/mg protein. One unit of neutral SMase hydrolyses 1 $\mu$mole of sphingomyelin per min at pH 7.4 at 37° C. One unit of acid SMase hydrolyzes 1 nmole of SM to N-acetylsphingosine and choline phosphate per hour at pH 5.0 at 7° C.

Preparation of a Cream and Treatment (Duration and Modality)

A cream was prepared (using a dehydrating base cream) containing sonicated lactic bacteria [2 20-g tubes of base cream plus 1 vial of sonicated lactic bacteria ($1 \times 10^{12}$ CFU) in 20 ml of water] and the effect of daily applications of the cream on the ceramide levels of the horny layer of the epidermis of the forearm was assayed in 8 volunteers as indicated in Table 1 here below.

TABLE 1

| No. | Sex | Age |
|-----|--------|-----|
| 1 | male | 45 |
| 2 | female | 39 |
| 3 | female | 29 |
| 4 | female | 27 |
| 5 | female | 33 |
| 6 | female | 32 |
| 7 | male | 38 |
| 8 | female | 25 |

The subject were instructed to self-administer the control cream and the experimental cream containing the lactic bacteria twice per day (approximately 1 ml, morning and evening). The control cream was applied daily on the right forearm, while the experimental cream was applied on the left forearm. Both creams were rubbed in until they were fully absorbed. Lipids of the horny layer of the epidermis were collected from the forearm by washing with 250 ml of 99.5% ethanol prior to the start of application of the cream (T0) and one week (T1) after the start of treatment. The ethanol extracts were concentrated with a rotary evaporator and then evaporated dry. The dried samples were dissolved in 2 ml of chloroform, dried with nitrogen and subjected to DAG kinase assay for ceramide quantification (Amersham, Buckinghamshire, Great Britain). After three extraction runs, the lipids were dried again with nitrogen, dissolved in 100 μl of chloroform and subjected to thin layer chromatography (TLC), using chloroform: methanol:acetic acid (65:15:5, v/v/v) as the run solvent. Phosphorylated ceramide was detected by autoradiography. The patches corresponding to ceramide-1-phosphate were cut and subjected to a count of the radioactivity present using scintillation liquid in a β-counter. The amount of ceramide present was determined on the basis of a standard curve obtained with authentic ceramide (type III; of bovine brain; Sigma Chemical Co., St. Louis, Mo.).

Results

Sphingomyelinase Activity in Lactic Bacteria

The levels of neutral sphingomyelinase activity in the sonicated lactic bacteria samples were approximately $2 \times 10^{-7}$ units/mg of bacteria. No acid sphingomyelinase activity was detected.

Effects of Sonicated Lactobacillus on Ceramide Levels in the Skin

The ceramide levels in the ethanol extracts obtained as described in the "Methods" section are given in Table 2 here below and the respective autoradiographs are shown in FIG. 1. It can be noted, regardless of the substantial subjective basal variability, that the use of both creams gave rise to an increase in ceramide levels in the forearm skin of all the subjects analyzed. However, the increase was much more marked and significant after application of the cream containing lactic bacteria. What is more, the effect of the experimental cream on ceramide levels could be detected earlier compared to that induce by the base cream, thus indicating faster action of the former.

TABLE 2

| No. | Right forearm | | Left forearm | |
|-----|------|------|------|------|
| | T0 | T1 | T0 | T1 |
| 1 | 0 | 0 | 0 | 1,941 |
| 2 | 223 | 567 | 147 | 298 |
| 3 | 8 | 500 | 24.2 | 700 |
| 4 | 8 | 347 | 2 | 300 |
| 5 | 300 | 500 | 435 | 1,390 |
| 6 | 400 | 480 | 236 | 340 |
| 7 | 30 | 28 | 180 | 270 |
| 8 | 10 | 280 | 12 | 278 |

What is claimed is:

1. A method of increasing the level of ceramides in the skin or mucosa comprising topically applying to the skin or mucosa a composition containing a sphingomyelinase obtained from lactic bacteria in the form of sonicated cells.

2. The method of claim 1 wherein the lactic bacteria is selected from the group consisting of *Lactobacillus acidophilus, Lactobacillus brevis, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus fermentum, Lactobacillus jensenii, Lactobacillus leichmanii, Lactobacillus minutus, Lactobacillus plantarum, Lactobacillus rogosae, Lactobacillus salivarius, Bifidobacterium adolescents, Bifidobacterium angulatum, Bifidobacteriumbifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum, Bifidobacterium pseudocatenulatum, Bifidobacterium pseudolongum, Streptococcus lactis, Streptococcus raffinolactis* and *Streptococcus thermophilus*.

3. The method of claim 1 wherein the composition contains $1 \times 10^2$ to $1 \times 10^{15}$ lactic bacteria per gram of composition.

FIG. 1. Autoradiographs of ceramide levels.

4. The method of claim 1 wherein the composition is in the form of the cosmetic composition in the form of a cream, ointment, emulsion, lotion, pearls, ovule, mascara, eyewash, toothpaste, mouthwash, lipstick, liposome, soap, shaving soap, tonics, douches, enteroclysis solution, shampoo, antidandruff preparation, impregnated and/or medicated bandage or gauze, transdermal gel or patch.

* * * * *